United States Patent [19]

Youngdale

[11] Patent Number: 4,645,766

[45] Date of Patent: Feb. 24, 1987

[54] 1,2-DIHYDRO-2-OXO-3-HYDROXYMETHYL PYRIDINES, COMPOSITIONS AND USE

[75] Inventor: Gilbert A. Youngdale, Portage, Mich.

[73] Assignee: The Upjohn Company, Kalamazoo, Mich.

[21] Appl. No.: 312,576

[22] Filed: Oct. 19, 1981

[51] Int. Cl.[4] ................... A61K 31/44; C07D 213/64
[52] U.S. Cl. ................... 514/345; 546/298; 546/301
[58] Field of Search ........ 546/301; 424/263; 514/345

[56] References Cited

U.S. PATENT DOCUMENTS

| | | | |
|---|---|---|---|
| 3,873,523 | 3/1975 | Doub et al. | 260/239.1 |
| 3,948,903 | 4/1976 | Doub et al. | 260/243 |
| 4,220,648 | 9/1980 | Youngdale | 424/266 |
| 4,275,069 | 6/1981 | Youngdale | 424/266 |
| 4,288,440 | 9/1981 | Youngdale | 424/263 |

OTHER PUBLICATIONS

Kutsky, *Handbook of Vitamins, Minerals and Hormones*, 2nd ed, (1981), pp. 233–241, 294, 295.
Rosenberg, *Chemistry and Physiology of the Vitamins*, (1945), pp. 197–216.
A. Dornnow: Uber Eine Direkte Synthese Von 3-Cyan-Pyridon-(2) und Seinem 6-Methyl-Derivat., Jahrg. Ber., 73: 153–156 (1940).
V. S. Fang, Salicylate Hypoglycemic Action in Alloxan-Diabetic Rats and Structural Relationships, Arch. Int. Pharmacodyn., 176: 193–208 (1968).
Gruber, W., et al., Montash., 81: 83–89 (1950).
Kochetkov, N. K., Chem. Abst., 47: 3309 (1953).
Mariella, R. P., Condensations of Unsymmetrical Ketones. I., JACS, 69: 2670–2672 (1947).
Mariella, R. P., et al., The Synthesis and Spectrum of 2-Cyclopropylpyridine, JACS, 70: 1494–1497 (1948).
Mariella, R. P., et al., Alpha-Oxygenated Pyridines. I., JACS, 73: 2616–2618 (1951).
Mariella, R. P., et al., Alpha-Oxygenated Pyridines. II., JACS, 74: 1915–1916 (1952).
Murakami, Y., et al., Synthesis of Organic Phosphates. III, Bull. Chem. Soc. Japan, 46: 2187–2190 (1973).

*Primary Examiner*—Robert W. Ramsuer
*Attorney, Agent, or Firm*—Robert A. Armitage

[57] ABSTRACT

The present invention relates to certain 1,2-dihydro-2-oxo-6-alkyl-3-pyridine carboxylic acids, carboxylate esters, and methanols, their preparation and their use as antihyperglycemic agents.

6 Claims, No Drawings

1,2-DIHYDRO-2-OXO-3-HYDROXYMETHYL PYRIDINES, COMPOSITIONS AND USE

DESCRIPTION

1. Technical Field

The present invention provides novel organic compounds. In particular, the present invention provides compounds structurally related to pyridine. Most particularly, the present invention relates to certain 1,2-dihydro-2-oxo-6-substituted-3-substituted-pyridine compounds.

The present invention further relates to novel methods for the synthesis and use of the novel organic compounds disclosed herein. These novel methods for use relate to the antihyperglycemic effect of administration of the novel organic compounds of the present invention.

The compounds of the present invention are derivatives of 1,2-dihydro-2-oxo-pyridine or 2-pyridinone. The structure and carbon atom numbering for this compound is indicated by Formula I. The compounds of the present invention have an alkyl group at the 6-position, a carboxylic acid, carboxylate ester or hydroxymethyl group at the 3-position, and a hydrogen, methyl or ethyl group at the 1-position.

The compounds can also be viewed as derivatives of 1,2-dihydro-2-oxo-nicotinic acid, shown in Formula II, which is the 3-carboxylic acid analog of 2-pyridinone (Formula I).

A derivative of 1,2-dihydro-2-oxo-nicotinic acid (Formula II), in which the nitrogen at the 1-position is protonated and the oxygen bonded to the carbon at the 2-position is in the keto-form, can also exist in a tautomeric form, in which the proton from said nitrogen is bonded instead to said oxygen. The tautomeric form is a derivative of 2-hydroxynicotinic acid.

In general, in any environment, both tautomeric forms are present, with the ratio of their concentrations dependent on the physical and chemical characteristics of the environment and the manner in which the derivative (in either form or any combination of the two forms) is introduced into the environment. In some situations, one tautomeric form can predominate to the exclusion or near exclusion of the other.

As indicated above, the present invention also relates to antihyperglycemic agents. Hyperglycemia refers to a condition commonly found in patients suffering from mature-onset diabetes mellitus and other diseases in which impairment of pancreatic function is a consequence thereof. Accordingly, hyperglycemic patients are those exhibiting elevated serum glucose levels. Failure to adequately control such elevated serum glucose levels has been associated in such patients with untoward cardiovascular effects (myocardioischemia, stroke, and peripheral vascular diseases), lethargy, coma, and even death.

While conventional treatment for these hyperglycemic conditions may include diet (e.g., restriction of carbohydrate intake) and insulin injection, one important means of treating such patients is with oral antihyperglycemic agents. The most important class of oral antihyperglycemic agents is sulfonylureas, e.g., tolbutamide, clorpropamide, tolazamide, and glyburide.

As oral antihyperglycemic agents, sulfonylureas have as a primary mechanism of action the induction of endogenous insulin release. Accordingly, these compounds exhibit activity in glucose-primed, fasted, intact rats and glucose-primed, fasted, adrenalectomized rats. However, in other animal preparations, e.g., alloxanized diabetic and eviscerate rats, no antihyperglycemic effect is observed.

Another class of oral antihyperglycemic agents is biguanidines, principally phenformin. Unlike the sulfonylureas, the biguanidines do not stimulate endogenous insulin secretion, but are nonetheless effective in lowering elevated blood glucose levels in mature-onset diabetics. In non-diabetic subjects, however, no significant antihyperglycemic effect is ordinarily observed upon biguanidine administration.

Yet another class of oral antihyperglycemic agents is represented by certain nicotinic acid derivatives, particularly 1,2-dihydro-2-oxo-nicotinic acid derivatives. Such compounds are, for example, disclosed in German Offenlegungsschrift No. 2,637,477, published Aug. 20, 1976, abstracted at Derwent Number 16112A. The tautomeric form of 1,2-dihydro-2-oxo-nicotinic acid, 2-hydroxynicotinic acid has been demonstrated to have antihyperglycemic activity in the alloxanized diabetic rat, but this activity has been associated with a decrease of plasma-free fatty acids. See Fang, V. S., Arch. Int. Pharmacodyn. 176,193 (1968).

2. Prior Art

Orally active antihyperglycemic agents are widely known in the art, as indicated by references cited above.

For example, see the references cited above relating to 1,2-dihydronicotinic acids. See, also, applicant's U.S. Pat. Nos. 4,220,648, 4,275,069, and 4,288,440 and the references cited therein.

Three 3-hydroxymethyl derivatives of 2-pyridinone are known. Murakami, Y. et al., Bull Chem. Soc. (Japan) 46, 2187 (1973), disclose 1,2dihydro-2-oxo-3-pyridinemethanol. Mariella, R. et al., JACS 73, 2616 (1951) disclose 4,6-dimethyl-1,2-dihydro-2-oxo-3-pyridinemethanol. Mariella, R. et al., JACS 74, 1915 (1952) disclose 6-methyl-1,2-dihydro-2-oxo-3-pyridinemethanol. The only one of these compounds for which any use is suggested is the 6-methyl derivative, for which Mariella et al. (JACS 74, 1915 (1952) report vitamin $B_6$ activity approximately 1/1000th that of the natural vitamin in an assay utilizing the mold *Neurospora sitophilia*. The 4,6-dimethyl derivative displayed neither vitamin $B_6$ activity nor anti-vitamin $B_6$ activity in the same assay. Mariella et al., JACS 73, 2616 (1951).

Numerous 1-alkyl-6-substituted-1,2-dihydro-2-oxo-3-pyridinecarboxylic acids and carboxylate esters are known, but no compounds of formula III, wherein $R_9$ is isobutyl or t-butyl; $R_{10}$ is methyl or ethyl; and $R_{12}$ is hydrogen or alkyl of 1-4 carbon atoms, inclusive, have been disclosed.

German Offenlegungsschrift No. 2,637,477, cited above, discloses generically numerous analogs of the compound of formula III, including ones in which $R_{12}$ is hydrogen or alkyl of 1-4 carbon atoms, inclusive, and $R_9$ is isobutyl and t-butyl. However, all analogs disclosed in the reference have substituents with $R_{10}$ containing at least 3 carbon atoms. In analogs specifically disclosed in the reference, $R_9$ is limited to hydrogen or methyl. The references recites that some of the compounds disclosed have antihyperglycemic activity, but it provides no information to suggest which of the compounds, among the many hundreds generically disclosed, have such activity.

U.S. Pat. No. 3,948,903 discloses analogs of the compound of formula III in which $R_{10}$ is hydrogen or methyl, $R_{12}$ is hyrogen, and $R_9$ is an aryl, cycloalkyl (with at least 5 carbon atoms in the ring), or heterocyclic group linked to the 2-pyrimidone ring through a methylene group. The patent discloses these analogs to be useful as intermediates in the synthesis of antibacterial compounds.

The subject matter of applicant's U.S. Pat. Nos. 4,220,648 and 4,275,069 is closely related to the subject matter of the present application. These patents disclose compounds of formula III wherein $R_9$ is —$CH_2C(CH_3)_2R_{13}$, wherein $R_{13}$ is alkyl of 1–4 carbon atoms, inclusive; $R_{10}$ is hydrogen; and $R_{12}$ is hydrogen or alkyl of 1–4 carbon atoms, inclusive. These compounds are disclosed to be useful as antihyperglycemic agents.

Applicant's U.S. Pat. No. 4,288,440 discloses antihyperglycemic 6-alkyl-1,2-dihydro-2-oxo-3-pyridinetetrazoles and 6-alkyl-1,2-dihydro-2-oxo-3-pyridinecarboxaldehydes.

Numerous other 6-alkyl-1,2-dihydro-2-oxonicotinic acids are known. Mariella R., JACS 69, 2670 (1947) reports 6-isobutyl-1,2-dihydro-2-oxo-nicotinic acid. Other known 6-alkyl-1,2-dihydro-2-oxo-nicotinic acids known include the 6-methyl compounds (Dornow, A., Ber. 73, 153 (1940)), the 6-propyl compound (Gruber, W., et al., Monatsh. 81, 83 (1950)), the 6-isopropyl and 6-n-pentyl compounds (Kochetkov. N. K., Doklady Akad. Nauk. USSR 84, 2289 (1952), Chem. Abstr. 47, 3309 (1953)), the 6-cyclopropyl compound (Mariella, R., et al., JACS 70, 1494 (1948)), and the 6-cyclohexyl compound (U.S. Pat. No. 3,873,523).

SUMMARY OF THE INVENTION

The present invention particularly relates to nove organic compounds.

The present invention further relates to the pharmacological use of such compounds.

The present invention further relates to novel pharmaceutical compositions employing these compounds. In particular, the present invention provides:

A. A compound of Formula IV wherein $R_1$ is hydrogen, methyl or ethyl;
wherein $R_3$ is —$CO_2R_4$ or —$CH_2OH$,
wherein $R_4$ is hydrogen or alkyl of 1 to 4 carbon atoms, inclusive:
wherein, when $R_1$ is not hydrogen, $R_6$ is isobutyl or t-butyl, and $R_3$ is —$CO_2R_4$;
wherein, when $R_1$ is hydrogen and $R_3$ is —$CO_2R_4$, $R_6$ is —$C(CH_3)_2R_7$,
wherein $R_7$ is alkyl of 1 to 3 carbon atoms, inclusive;
wherein, when $R_1$ is hydrogen and $R_3$ is —$CH_2OH$, $R_6$ is —$CH_2C(CH_3)_2R_8$,
wherein $R_8$ is hydrogen, methyl or ethyl;
or a pharmacologically acceptable salt thereof.

B. A method of treating adult onset diabetes mellitus in a human suffering from said disease which comprises orally administering an amount of a compound of Formula IV, or a pharmacologically acceptable salt thereof, wherein $R_1$, $R_3$ and $R_6$ are defined as above, effective to exert a predetermined systemic antihyperglycemic effect.

C. An oral pharmaceutical composition in unit dosage form comprising an amount of a compound of Formula IV wherein $R_1$, $R_3$ and $R_6$ are as defined above, sufficient to provide an antihyperglycemic effect in an adult-onset diabetic human to whom said composition is administered, and a suitable pharmaceutical carrier.

In this specification, "alkyl of 1 to 3 carbon atoms, inclusive" means methyl, ethyl, n-propyl or isopropyl and "alkyl of 1 to 4 carbon atoms, inclusive" means methyl, ethyl, n-propyl, isopropyl, n-butyl, isobutyl, (1-methyl)propyl or t-butyl.

When $R_4$ in a compound of Formula IV within the scope of this invention is (1-methyl)propyl, the compound will exist in two forms related as enantiomers: Both enantiomers, separately in pure form or in any combination, are within the scope of the invention.

The novel compounds of the present invention are all antihyperglycemic agents, particularly oral antihyperglycemic agents. This antihyperglycemic activity renders these compounds useful in the treatment of adult-onset diabetes mellitus. Adult-onset diabetes mellitus is a disease characterized by pancreatic dysfunction resulting in insufficient levels of insulin being produced or secreted by the pancreas. This form of diabetes mellitus is distinguished from other pancreatic disorders wherein the capacity of the pancreas to produce insulin is totally abolished. While oral antihyperglycemic agents are uniformly ineffective in treating the latter pancreatic diseases, well-known and well-recognized methods exist in the art for the treatment of adult-onset diabetes mellitus with oral antihyperglycemic agents.

The novel compounds of the present invention are all used in the treatment of adult-onset diabetes mellitus by these well-known and well-recognized methods in the art. Accordingly, a patient to be treated with the novel compounds of the instant invention is first diagnosed as a diabetic by conventional means (e.g., the persistence of elevated serum glucose levels), and a treatment regimen with the compounds of the present invention is established so that the elevation in a patient's serum glucose level is either significantly reduced or eliminated. Precise therapeutic endpoint of the treatment (i.e., elimination or merely reduction in hyperglycemia) is readily determined by the attending physician based upon the clinical presentation and concomitantly employed treatment. For example, the novel compounds of the instant invention may be employed to significantly reduce hyperglycemia in a patient, with a carbohydrate-restricted diet providing the further measure of control.

While the novel compounds of the instant invention may be administered by any convenient systemic route, these compounds are most significantly and usefully employed as oral antihyperglycemic agents, particularly in solid dosage forms (e.g., capsules and tablets). Alternatively, liquid oral dosage forms (e.g., syrups and elixirs) are alternatively employed. The solid, oral pharmaceutical compositions in accordance with the present invention are all prepared by methods known in the art, e.g., methods for preparing other oral antidiabetic compositions. These pharmaceutical compositions are all prepared by methods well known in the art.

Since an individual patient response to treatment with compounds in accordance with the present invention may vary, effective dosages of the compounds of the instant invention will vary from patient to patient. Ordinarily, an oral dosage of 1 mg/kg of a compound in accordance with the instant invention will be adequate to significantly reduce hyperglycemia in patients being treated. Repeated dosages (e.g., every four to twelve hours) may be required during the day to maintain the antihyperglycemic effect. Accordingly, dosages in accordance with the present invention may range from as low as about 0.1 mg/kg/dose to as high as about 10 mg/kg/dose, depending upon the patient, frequency of treatment, and observed response. In accordance with well recognized methods, an attending physician may at first prescribe a relatively small amount of the novel 1,2-dihydro-2-oxo-6-alkyl-3-pyridinecarboxylic acid, carboxylate ester or hydroxymethyl derivative with subsequent increases in this dosage as necessary to achieve the desired level of control.

The antihyperglycemic activity of a compound is established by testing the compound in rats as presently described:

Test animals are Sprague-Dawley derived, pathogen-free, female rats weighing 115–125 gm. Test vehicle is sterile 0.5% carboxymethylcellulose in saline. Groups of eight rats serve as control groups. Groups of four rats serve as test groups. Rats in control and test groups are fasted for 18 to 24 hours prior to being administered 125 mg glucose in 1 ml of 0.9% saline by subcutaneous injection. Immediately before administration of glucose, rats in a test group are given, orally, test compound at a selected dosage in 0.5 cm$^3$ of test vehicle while rats in a control group are given 0.5 cm$^3$ of vehicle only. Two hours after injection of glucose, rats are bled via the vena cava while under Cyclopal ® (5-allyl-5-(2-cyclopenten-1-yl)barbituric acid) anesthesia and the blood sugars are determined.

Initially, a compound is tested twice at a dosage of 100 mg/kg. A compound is considered active if, at this dosage, in each test, the ratio of the mean blood sugar of rats in the test group to that of rats in the control group is less than 0.87 and if the product of these ratios from both tests is less than 0.65. This criterion for determining activity is based on the blood-sugar lowering effect in such tests of tolbutamide, a known antihyperglycemic agent used for treating adult-onset diabetes mellitus.

By testing a compound in the same way at successively lower doses and comparing its blood-sugar lowering effect at each dose with that of tolbutamide at various doses, the antihyperglycemic potency of a compound relative to that of tolbutamide is evaluated.

The novel 6-alkyl-1,2-dihydro-2-oxo-3-carboxylic acid, carboxylate ester, or hydroxymethyl derivatives of the present invention are synthesized starting with the corresponding 3-pyridinecarbonitriles of formula V. These 3-pyridine-carbonitriles can be prepared as indicated in Chart A from the appropriate ketone of formula VI via the alkanaldehyde sodium salt of formula VII. The preferred method of preparing compounds of formula VII, by reacting those of formula VI with ethyl formate and sodium hydride in toluene in the presence of a small amount of absolute ethanol, is descriged in detail in applicant's U.S. Pat. No. 4,220,648. Procedures for synthesizing compounds of formula V from those of formula VII by (A) refluxing the formula VII compound with cyanoacetamide in dioxane followed by acidification with aqueous acetic acid or (B) refluxing the formula VII compound with cyanoacetamide in pyridine followed by acidification with concentrated sulfuric acid are also described in detail in U.S. Pat. No. 4,220,648. Another procedure for synthesizing compounds of Formula V is illustrated in Chart B and described in detail in Preparation 1 below. In the process of Chart B, the appropriate ketone of Formula VI is heated with N,N-dimethylformamidedimethylacetal in the presence of DBU (1,8-diazabicyclo[5.4.0]undec-7-ene) with occasional removal of methanol to form the 1-dimethylamino-3-oxo-alkene of Formula XXIV. The compound of Formula XXIV is then refluxed with two equivalents of cyanoacetamide in a mixture of water and acetonitrile to yield the 3-pyridine carbonitrile of Formula V. Compounds of formula V are known. For example: R. P. Mariella, JACS 69, 2670 (1947); W. Barbieri and L. Bernardi, Tetrahedron 21, 2453 (1965); J. C. Martin, et al., J. Org. Chem. 31, 943 (1966); R. H. Hasek, et al., J. Org. Chem. 28, 1468 (1963).

Compounds of formula IV, in which $R_1$ is not hydrogen, are prepared from the corresponding 1-alkyl-1,2-dihydro-2-oxo-3-pyridinecarbonitriles of formula VIII, wherein $R_{14}$ is methyl or ethyl. Compounds of formula VIII are prepared from the corresponding 1,2-dihydro-2-oxo-3-pyridinecarbonitriles of formula V as indicated in Chart C. In the process of Chart C, the compound of formula V is reacted with the appropriate dialkyl sulfate in 2N aqueous sodium hydroxide to produce the corresponding compound of formula VIII. This process is described in more detail in Example 5(A).

As indicated in Chart D, the 6-alkyl-1,2-dihydro-2-oxo-3-pyridinecarbonitriles of formulas V and VIII are converted to the corresponding 3-pyridine carboxylic acids of formula IX. This conversion can be done by acid hydrolysis with concentrated hydrochloric or sulfuric acid or basic hydrolysis with concentrated aqueous sodium hydroxide or concentrated aqueous potassium hydroxide with ethanol. Alternatively, as indicated in Chart E, the compounds of formulas V or VIII can be converted to the corresponding acids of formula IX via the alkyl 1,2-dihydro-2-oxo-6-alkyl-3-pyridinecarboximidate of formula X, wherein $R_{15}$ is alkyl of 1–4 carbon atoms, inclusive. The imidate ester is formed by reacting the compound of formula V or VIII with anhydrous HCl in absolute alkanol of formula $R_{15}OH$. The imidate is then hydrolyzed to the acid of formula IX by boiling in water.

It has been found that the most advantageous method for hydrolyzing a nitrile of formula V or VIII to the corresponding acid of formula IX varies from nitrile to nitrile. The preferred methods are acid hydrolysis by heating at approximately 125° C. in 90% aqueous $H_2SO_4$ and basic hydrolysis in concentrated aqueous NaOH or ethanolic KOH.

Chart F shows that the 6-alkyl-1,2-dihydro-2-oxo-3-pyridinecarboxylate esters of formula XI can be synthesized directly from the corresponding acids of formula IX by well-known esterification techniques, including reaction of the acid with a diazoalkane of formula $R_{16}CHN_2$, wherein $R_{16}$ is hydrogen or alkyl of 1–3 carbon atoms, inclusive, such that $R_{16}CH_2$ is $R_4$, and acid-catalyzed esterification with the alkanol of formula $R_4OH$.

Chart G shows that the esters of formula XI can also be synthesized from the corresponding nitriles of formula V or VIII via the 6-alkyl-1,2-dihydro-2-oxo-3-pyridinecarboximidate esters of formula XII. The process of synthesizing the compounds of formula XII from those of formula V or VIII and alkanol of formula $R_4OH$ is described above in connection with the process illustrated in Chart E. The compounds of formula XII, in aqueous solution at room temperature, transform spontaneously to the esters of formula XI on standing for long periods (several hours to several days).

Chart H shows the esterification of the acids of formula IX through the acid chloride intermediates of formula XIII. The acid chloride intermediates are formed by heating the acids in toluene in the presence of oxalyl chloride. The acid chloride intermediates are then transformed to the esters of formula XI by heating in the presence of absolute alkanol of formula $R_4OH$. The preferred method for synthesizing the esters of formula XI from the acids of formula IX is that illustrated in Chart H.

The preferred method of obtaining esters of formula XI from nitriles of formulas V or VIII is to first synthesize the acid of formula IX and then esterify the acid by the method illustrated in Chart H.

Chart I illustrates the synthesis of 6-alkyl-1,2-dihydro-2-oxo-3-pyridinemethanols from the corresponding 3-pyridinecarbonitriles of Formula V. The first step in the process illustrated in Chart I, the synthesis of the 6-alkyl-1,2-dihydro-2-oxo-3-pyridinecarboxaldehyde of Formula XXVI from the corresponding 3-pyridinecarbonitrile of Formula V, is described in detail in applicant's U.S. Pat. No. 4,288,440. This first step involves reaction of the compound of Formula V in the presence of Raney nickel catalyst with (A) formic acid, or (B) sodium hypophosphite in aqueous acetic acid in pyridine. The second step in the process illustrated in Chart I, the reduction of the 1,2-dihydro-2-oxo-3-pyridinecarboxaldehyde of Formula XXVI to the 1,2-dihydro-2-oxo-3-pyridinemethanol of Formula XXV, can be accomplished by reduction with a reducing agent of appropriate strength to selectively reduce the aldehyde group at the 3-position on the compound of Formula XXVI. Such reducing agents include sodium borohydride, lithium tri-t-butoxyaluminum hydride and the like.

Another method, and the preferred method, for carrying out the reduction of compound of Formula XXVI to those of Formula XXV, illustrated as the second step in Chart I, is hydrogenolysis in ethanol in the presence of palladium-on-charcoal.

Especially preferred among the novel compounds of the present invention are the 1,2-dihydro-2-oxo-3-pyridine derivatives of Formula XXV, and most especially preferred among the derivatives of Formula XXV is the 6-neopentyl derivative.

A compound of formulas IX is transformed to a pharmacologically acceptable salt by neutralization with base corresponding to the salt.

Salts in accordance with the present invention include pharmacologically acceptable metal cations, amine cations and quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention. Most especially preferred among the metal cations is that derived from sodium.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-propanol, tris(hydroxymethyl)aminomethane, N-phenylethanolamine, N-(p-tert-amyl)phenyldiethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

PREPARATION 1

1,2-Dihydro-2-oxo-6-neopentyl-3-pyridine carbonitrile (Compound of Formula V in which $R_6$ is neopentyl)

A. 1-Dimethylamino-3-oxo-5,5-dimethylhex-1-ene (Compound of Formula XXIV in which $R_6$ is neopentyl)

A mixture of 50 ml (0.355 mol) of 2,2-dimethyl-4-pentanone, 55 ml (0.415 mol) of N,N-dimethylformamide dimethylacetal, and 0.5 ml of DBU (1,8-diazabicyclo[5.4.0]undec-7-ene) in a flask equipped with a 6-inch Vigreux column with attached distillation head is heated at 135°–145° C. (i.e., oil bath temperature) for 3 days. The methanol which forms is allowed to distill off occasionally. The temperature of the distillate is not allowed to exceed 65° C. After the three days, the temperature of the oil bath is gradually raised to 180° C. over 4.5 hours, during which the temperature of the distillate does not exceed 65° C. A total of 30 ml of distillate is collected. The pressure is lowered and a forerun is collected. Then the product is distilled at 140°–143° C. at 5 mm Hg pressure. 55.72 gm of oil, which rapidly solidifies, is obtained from this distillation. The oil tends to solidify in the distillation head. Silica gel thin-layer chromatography (1×4″) (40% acetone-methylene chloride) shows minor impurities. A 10 gm portion of the distilled product is chromatographed on a 400 gm column of silica gel. The column is eluted with 30% acetone-methylene chloride and 200 ml fractions are collected. The fractions are assayed by silica gel thin-layer chromatography (1×4″) (40% acetone-methylene chloride). Fractions 7–16 are combined and yield 9.34 gm of solid. The solid is crystallized from ether-hexane, which yields 8.9 gm of product as plates. Melting Point: 72°–74° C. A Carbon:Hydrogen:Nitrogen analysis shows: 71.05% C; 11.36% H; 8.23% N. Mass Spectrum of the product reveals ions (m/e) at 169 (molecular), 154, 113, 112, 99, 98, 96, 71, 70, 55, and 42. NMR Spectrum of the product in $CDCl_3$ has the following peaks (positions in δ): 1.0 (s, 9H), 2.2 (s, 2H), 2.9 (s, 6H), 5.0 (d, J=12 Hz, 1H), 7.48 (d, J=12 Hz, 1H). Infrared spectrum (mull) shows peaks at 1645, 1583, 1551 $cm^{-1}$.

B. 1,2-Dihydro-2-oxo-6-neopentyl-3-pyridinecarbonitrile

A mixture of 7.9 gm (0.047 mol) of the product of Preparation 1(A) and 7.9 gm (0.094 mol) of cyanoacetamide in 10 ml of water and 90 ml of acetonitrile is refluxed for 4 days. The solvent is evaporated leaving a semi-solid mass. The material is slurried with 50 ml of water. The solid is collected by filtration, washed with water, and dried giving 6.4 gm of solid. The solid is chromatographed on a 400 gm column of silica gel. The column is eluted with 7.5% acetone-methylene chloride and 200 ml fractions are collected. The fractions are assayed by silica gel thin-layer chromatography (1×4") (20% acetone-methylene chloride). Fractions 9-24 are combined and crystallized from methylene chloride-Skellysolve B yielding 4.51 gm (0.0237 mol) of title product as small needles. Yield: 51%. Melting Point: 211°-212.5° C. The melting point of a mixture of the product of this procedure and title product obtained by the procedure detailed in Example 1(B) of U.S. Pat. No. 4,220,648 is also 211°-212.5° C.

DESCRIPTION OF THE PREFERRED EMBODIMENTS

Compounds of the instant invention are prepared in accordance with the representative examples provided below:

EXAMPLE 1

6-Tert-butyl-1,2-dihydro-2-oxo-3-pyridinecarboxylic acid (Compound of Formula IX in which $R_1$ is hydrogen and $R_6$ is tert-butyl)

A mixture of 14 gm (0.079 moles) of 6-tert-butyl-1,2-dihydro-2-oxo-3-pyridinecarbonitrile and a solution of 20 gm of potassium hydroxide in 250 ml of 80% aqueous ethanol is refluxed for 19 hr. The solvent is evaporated. The residue is dissolved in 250 ml water, cooled in an ice bath, and acidified with concentrated hydrochloric acid. The solid is collected by filtration, washed well with water and air-dried, giving 12.8 gm of solid. Thin-layer chromatography shows the solid contains a large proportion of the 3-pyridinecarbonitrile starting material. The solid and 150 ml of 20% aqueous sodium hydroxide is refluxed for 16 hr. Upon cooling, crystals separate. The mixture is diluted with 300 ml water, which causes the solid to dissolve. The solution is cooled in an ice bath and acidified with concentrated hydrochloric acid. The solid which precipitates is collected by filtration, washed well with water, and dried under vacuum at 55° C. overnight, giving 13.3 gm of solid. The solid is warmed in methanol-ethanol-tetrahydrofuran. The hot mixture is filtered to remove some insoluble material. Water is added to the warm filtrate. Cooling gives 12 gm (0.061 moles) of the title compound as white needles. Yield: 78%. Melting point: 254°-257° C. Carbon:Hydrogen:Nitrogen analysis of the product shows: 61.75% C, 6.68% H, and 7.27% N. Mass spectrum of the product reveals ions (m/e) at 195 (molecular), 162, 152, 151, 150, 136, 134, 108, 41, and 39. NMR spectrum of the product in (DMSOd$_6$) has the following peaks (positions in $\delta$): 1.3 (s, 9H), 6.6 (d, J=8 Hz, 1H), 8.29 (d, J=8 Hz, 1H), 14.5-14.78 (br, 1H). Infrared spectrum (mull) shows peaks at 3230, 3060, 2660, 1750, 1715, 1630, 1600, 1555, 1495, 1335, 1270, 1150, 975, 910, and 795 cm$^{-1}$. In the assay of antihyperglycemic activity described above, the compound is found to be active.

EXAMPLE 2

6-(1,1-Dimethyl)propyl-1,2-dihydro-2-oxo-3-pyridinecarboxylic acid (Compound of Formula IX in which $R_1$ is hydrogen and $R_6$ is 1,1-dimethylpropyl)

2.5 gm (0.012 mole) of 6-(1,1-dimethyl)propyl-1,2-dihydro-2-oxo-3-pyridinecarbonitrile is suspended in 25 ml of 90% aqueous sulfuric acid. The suspension is heated at 120° C. for 21 hr. After this time, water is added to the solution and a precipitate develops. The precipitate is filtered and then dissolved in acetone, and Norit is added. The suspension is filtered and the solvent removed under reduced pressure to yield solid. This solid is dissolved in methylene chloride, and then hexane is added. A solid precipitates. This solid is filtered. After drying the solid overnight in a vacuum oven, 1.2 gm (0.0057 moles) of the title product is obtained as a solid. Yield: 48%. Melting point: 148°-153° C. Carbon:Hydrogen:Nitrogen analysis of the product shows 62.83% C, 7.20% H, and 6.80% N. Mass spectrum of the product reveals ions (m/e) at 209 (molecular), 165, 166, 162, 136, 163, 181, 176, 39, and 79. NMR spectrum of the product in CDCl$_3$ has the following peaks: (positions in $\delta$) 0.80 (t, J=6 Hz, 3H); 1.45 (s, 6H); 1.85 (quart, J=6 Hz, 2H); 6.65 (d, J=5 Hz, 2H); 8.8 (d, J=5 Hz, 2H); 12.31 (s(br), 1H). Infrared spectrum (mull) shows peaks at 3050, 2715, 1738, 1680, 1674, 1627, 1594, and 1555 cm$^{-1}$. In the assay of antihyperglycemic activity described above, the compound is found to be active.

EXAMPLE 3

6-Tert-butyl-1,2-dihydro-2-oxo-3-pyridinecarboxylic acid methyl ester (Compound of Formula XI in which $R_1$ is hydrogen, $R_4$ is methyl, and $R_6$ is tert-butyl)

1.0 gm (0.0051 moles) of the product of Example 1 is suspended in 20 ml of toluene. Oxalyl chloride (4.5 ml, 0.058 moles) is then added. The suspension is heated to 90° C. After 10 min at 90° C., all solid is dissolved. Heating at 90° C. continues for 3 hr. The solvent is then removed under reduced pressure. The resultant oil is then diluted with 10 ml of toluene, and the solvent is removed under reduced pressure a second time. This gives 0.9 gm of the acid chloride intermediate as an oil. This oil is then diluted with 20 ml of methanol. The resultant solution is heated at reflux for 0.5 hr. Removal of solvent leads to an oil which soon solidifies. This solid is dissolved in 15 ml of methylene chloride, and 45 ml of Skellysolve B is added. A solid (needles) is deposited and filtered. Evaporation of the solvents, using a stream of air, gives a second crop of needles. Drying of the two crops produces 0.3 gm and 0.2 gm, respectively, of the title product as needles. Yield: 0.002 moles, 40%. Melting point: 171°-174° C. Carbon:Hydrogen:Nitrogen analysis of the product shows: 61.96% C, 7.24% H, and 6.53% N. Mass spectrum of the product reveals ions (m/e) at 209 (molecular), 194, 178, 177, 176, 163, 162, 135, 79, and 39. NMR spectrum of the product in CDCl$_3$ has the following peaks (positions in $\delta$): 1.5 (s, 9H), 3.95 (s, 3H), 7.65 (d, J=7.5 Hz, 1H), 8.3 (d, J=7.5 Hz, 1H), 12.4 (s, 1H). Infrared spectrum (mull) shows peaks at 3160, 3080, 3000, 1750, 1700, 1655, 1590, 1570, 1485, 1290, 1150, 1120, 1075, 785 cm$^{-1}$. In the assay of antihyperglycemic activity described above, the compound is found to be active.

EXAMPLE 4

6-Tert-butyl-1,2-dihydro-2-oxo-3-pyridinecarboxylic acid ethyl ester (Compound of Formula XI in which $R_1$ is hydrogen, $R_4$ is ethyl, and $R_6$ is tert-butyl)

9.8 gm (0.05 moles) of the title product of Example 1 is suspended in 200 ml of toluene. Oxalyl chloride (45 ml, 0.58 moles) is then added. The mixture is heated and stirred for 3 hr. After this time, the solvent is removed from the solution. The oil which remains is diluted with 20 ml of toluene. This toluene is then removed under reduced pressure. The process (addition and removal of toluene) is repeated a second time, yielding 10.3 gm of the intermediate acid chloride as an oil. The oil is then diluted with 250 ml of absolute ethanol, whereupon a vigorous reaction commences. After the reaction has subsided, the mixture is heated to reflux (90° C.) for 45 min. The solvent is removed under reduced pressure and yields 16 gm of a solid. This solid is dissolved in 40 ml of methylene chloride, to which 60 ml of Skellysolve B is added. A needle-like solid precipitates and is filtered to yield title product. Evaporation of solvents (using an air stream) produces four crops of product. These four crops are individually dried and yield 3.5 gm, 2.50 gm, 0.225 gm, and 0.800 gm of title product, respectively. Total yield: 7.0 gm, 0.031 moles, 62%. Melting point: 118°–120° C. NMR spectrum of the product in $CDCl_3$ has the following peaks (positions in δ): 1.45 (s+triplet, 12H), 4.35 (quartet, J=7.5 Hz, 2H), 6.25 (d, J=7 Hz, 1H), 8.2 (d, J=7 Hz, 1H), 11.75 (s(br), 1H). In the assay of antihyperglycemic activity described above, the compound is found to be active.

EXAMPLE 5

1-Methyl-6-isobutyl-1,2-dihydro-2-oxo-3-pyridinecarboxylic acid (Compound of Formula IX in which $R_1$ is methyl and $R_6$ is isobutyl)

A. 1-Methyl-6-isobutyl-1,2-dihydro-2-oxo-3-pyridine carbonitrile (Compound of Formula VIII in which $R_{14}$ is methyl and $R_6$ is isobutyl).

To a stirred solution of 35.1 gm (0.199 moles) of 6-isobutyl-1,2-dihydro-2-oxo-3-pyridinecarbonitrile and 80 gm (2 moles) of sodium hydroxide in 1 liter of water is added 95 ml (1.0 moles) of dimethyl sulfate dropwise over 15 min. After the addition is complete, the mixture is heated on a steam bath for 5 min. The cooled mixture is extracted with ethyl acetate (3×200 ml). The combined extracts are washed with 75 ml of brine and dried over magnesium sulfate. Evaporation of solvent leaves 29.6 gm of oil. The oil is chromatographed on a 1.2 kg column of silica gel. The column is eluted with 5% acetone-methylene chloride and 200 ml fractions are collected. The fractions are assayed by silica gel thin-layer chromatography (1×4") (10% acetone-methylene chloride). Fractions 18–41 are combined and crystallized with acetone-hexane, yielding 18.05 gm (0.095 moles) of title product as needles. Yield: 47.7%. Melting point: 97°–100° C. A portion is recrystallized from acetonehexane affording needles with melting point 97.5°–99.5° C. Carbon:Hydrogen:Nitrogen analysis shows 69.16% C, 7.36% H, 14.76% N. Mass spectrum of the product reveals ions (m/e) at 190 (molecular), 175, 148, 120, 119, 86, 64, 43, 41, and 28. NMR spectrum of the product in $CDCl_3$ has the following peaks (positions in δ): 1.0 (d, J=6 Hz, 6H), 1.68–2.25 (multiplet, 1H), 2.6 (d, J=7 Hz, 2H), 3.55 (s, 3H), 6.12 (d, J=7 Hz, 1H), 7.72 (d, J=7 Hz, 1H). Infrared spectrum (mull) shows peaks at 2220, 1645, 1560, 770 $cm^{-1}$.

b.
1-Methyl-6-isobutyl-1,2-dihydro-2-oxo-3-pyridinecarboxylic acid

A mixture of 17.55 gm (0.0923 moles) of the product of Example 5(A) and a solution of 20 gm of potassium hydroxide in 300 ml of 80% aqueous ethanol is refluxed for 20 hr. The solvent is evaporated. The residue is treated with 250 ml of water. 250 ml of ethyl acetate is combined with the aqueous solution and the small amount of solid which does not dissolve in the water, and the mixture is shaken. The aqueous layer is cooled in an ice bath and acidified with concentrated hydrochloric acid. A solid separates. The mixture of solid and aqueous solution is extracted with ethyl acetate (3×150 ml). The three extracts are combined and washed with 50 ml of water and 50 ml of brine and dried over magnesium sulfate. Evaporation of the solvent leaves 17.55 gm of solid which is crystallized twice from acetonehexane yielding 14.8 gm (0.071 moles) of the title product as needles. Yield: 76.7%. Melting point: 118°–119° C. Carbon:Hydrogen:Nitrogen analysis shows 63.48% C; 7.08% H; 6.72% N. Mass spectrum of the product reveals ions (m/e) at 210, 209 (molecular), 176, 166, 165, 150, 149, 138, 94, 93, and 39. NMR spectrum of the product in $CDCl_3$ has the following peaks (positions in δ): 1.02 (d, J=6 Hz, 6H), 1.65–2.4 (multiplet, 1H), 2.65 (d, J=7 Hz, 2H), 3.68 (s, 3H), 6.42 (d, J=8 Hz, 1H), 8.34 (d, J=8 Hz, 1H), 14.46 (s, 1H). Infrared spectrum (mull) shows peaks at 2720, 1730, 1620, 1580, 1545, 1485, 1130, 935, and 795 $cm^{-1}$. In the assay of antihyperglycemic activity described above, the compound is found to be active.

EXAMPLE 6

6-Neopentyl-1,2-dihydro-2-oxo-3-pyridinemethanol (Compound of Formula XXV in which $R_6$ is neopentyl)

A mixture of 3.00 gm (0.0154 moles) of 1,2-dihydro-2-oxo-6-neopentyl-3-pyridinecarboxaldehyde, 0.3 gm of 10% palladium-on-charcoal, and 150 ml of ethanol is shaken in a Parr apparatus, with an initial hydrogen presence of 3.14 l bars, for 6 hours. During the last 2 hours of shaking, the hydrogen pressure in the apparatus remains constant at 1.72 bars. The catalyst is removed by filtration. Evaporation of solvent leaves 2.94 gm of solid, which is recrystallized from methylene chloride-hexane to yield, upon filtration, 2.27 gm of small needles. Evaporation of the methylene chloride-hexane from the filtrate leaves 0.51 gm of sticky solid. The 2.27 gm and 0.51 gm crops are combined and dissolved in 50 ml of 5% methanol in methylene chloride. The solution is applied to a 400 g column of silica gel, which is eluted with 5% methanol-methylene chloride. 200 ml fractions are collected. The fractions are assayed by silica gel thin-layer chromatography (1×4") (10% methanol-methylene chloride). Fractions 13–23 are combined and crystallized from methylene chloride-hexane, yielding 2.2 gm (0.011 moles) of small needles. Yield: 73%. Melting Point: 157°–159° C. Carbon:Hydrogen:Nitrogen analysis of the product reveals 67.32% C; 8.78% H, and 7.13% N. Mass Spectrum of the product shows ions at (m/e): 195 (molecular), 180, 166, 139, 128, 122, 121, 109, 93, 57, and 41. NMR Spectrum of the product in $CDCl_3$ shows peaks at (position in δ): 0.99 (s, 9H), 2.49 (s. 2H). 3.93–4.29 (broad, 1H), 4.6 (s, 2H), 6.05 (d, J=7.5 Hz, 1H), 7.38 (d, J=7.5 Hz, 1H), 12.7–13.1 (broad, 1H). Infrared spectrum (mull) has peaks at 3431, 3299, 3135, 3028, ~2800 (broad). 1639 (shoulder), 1634, 1572, 1050, 1014, and 979 $cm^{-1}$. In the assay of antihyperglycemic activity described above, the title product is found to have a potency of 5×tolbutamide.

FORMULAS
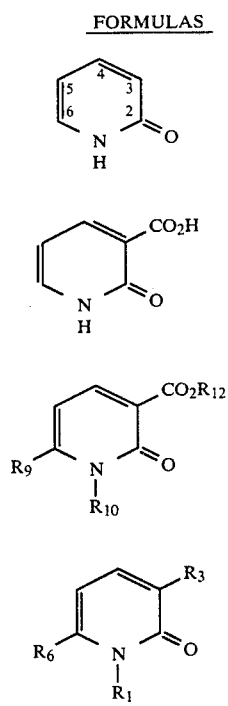
I
II
III
IV
CHART A
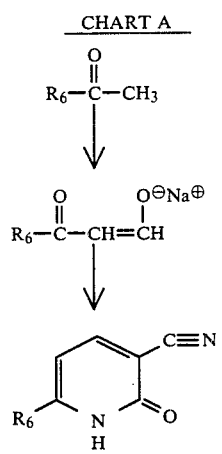
CHART B
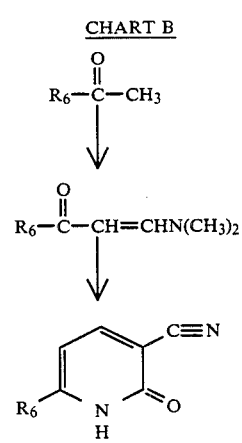
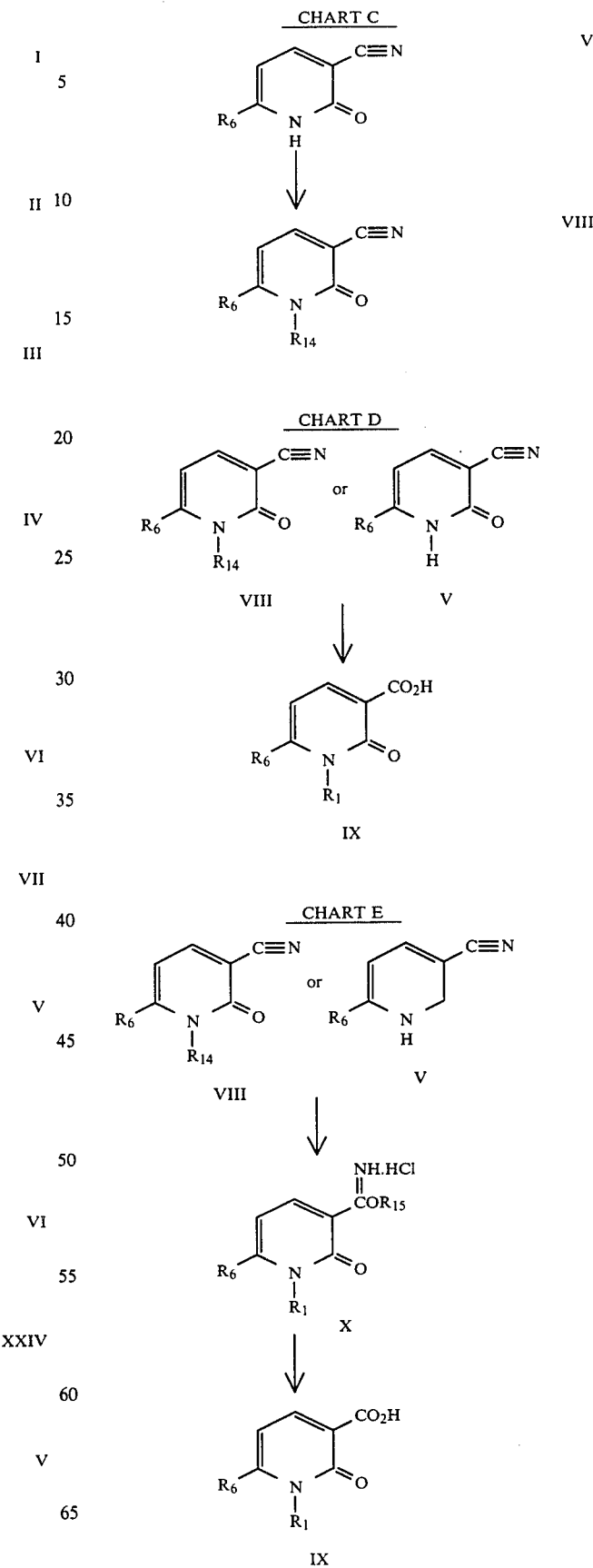
V
VIII
VI
IX
V
X
IX

CHART F

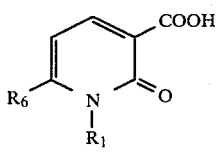 IX

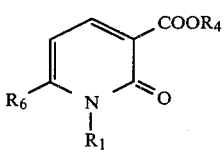 XI

CHART G

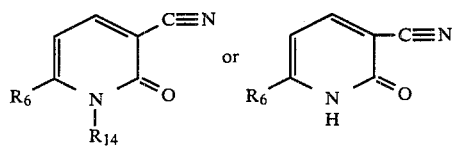
VIII    V

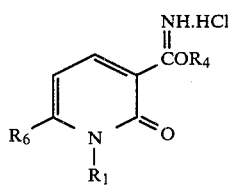 XII

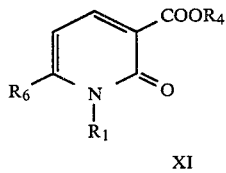 XI

CHART H

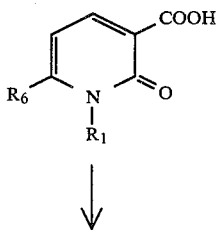 IX

-continued
CHART H

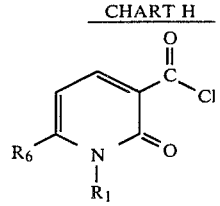 XIII

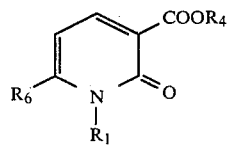 XI

CHART I

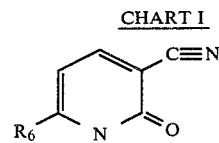 V

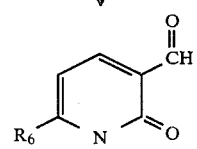 XXVI

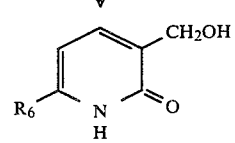 XXV

What is claimed is:
1. A compound of formula IV

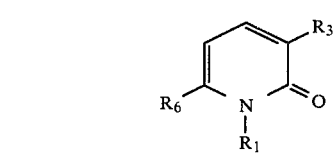 VI wherein $R_1$ is hydrogen;
wherein $R_3$ is —CH$_2$OH;
wherein $R_6$ is —CH$_2$C(CH$_3$)$_2$R$_8$, wherein $R_8$ is hydrogen, methyl or ethyl; or
a pharmacologically acceptable salt thereof.
2. 1,2-Dihydro-2-oxo-6-neopentyl-3-pyridinemethanol, a compound according to claim 1 wherein $R_8$ is methyl.
3. A method of treating adult-onset diabetes mellitus in a human suffering from said disease which comprises orally administering an amount of a compound of Formula IV

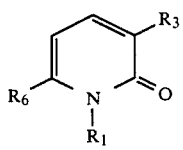

wherein $R_1$, $R_3$ and $R_6$ are as defined in claim 1, or a pharmacologically acceptable salt thereof, effective to exert a predetermined systemic antihyperglycemic effect.

4. A method according to claim 3 wherein said compound is 1,2-dihydro-2-oxo-6-neopentyl-3-pyridinemethanol.

5. An oral pharmaceutical composition in unit dosage form comprising an amount of a compound of Formula IV

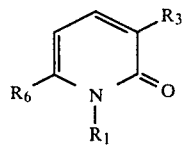

wherein $R_1$, $R_3$ and $R_6$ are as defined in claim 1, or a pharmacologically acceptable salt thereof, sufficient to provide an antihyperglycemic effect in an adult-onset diabetic human to whom said composition is administered and a suitable pharmaceutical carrier.

6. A composition according to claim 5 wherein said compound is 1,2-dihydro-2-oxo-6-neopentyl-3-pyridinemethanol.

* * * * *

UNITED STATES PATENT OFFICE
CERTIFICATE OF CORRECTION

Patent No. 4,645,766                                   Dated February 24, 1987

Inventor(s) Gilbert A. Youngdale

It is certified that error appears in the above-identified patent and that said Letters Patent are hereby corrected as shown below:

Patent Reads:

Column 3, Line 37, "relates to nove"
Column 5, Line 53 "is descriged"
Column 12, Line 36 "3.14 I bars,"
Column 14, Line 44, in Chart E

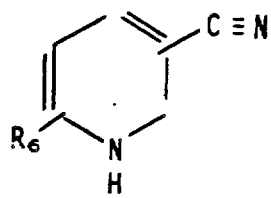

Column 16, Line 50, "VI"
Column 17, Line 4, "VI"
Column 18, Line 6, "VI"

Case Reads:

Page 4, Line 24 --relates to novel--
Page 8, Line 2 --is described--
Page 17, Line 3 --3.14 bars,--
Page 23, Line 9, in Chart E

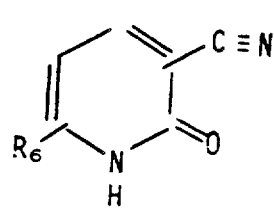

Page 28, Line 9, --IV--
Page 29, Line 26, --IV--
Page 30, Line 23, --IV--

Signed and Sealed this

Sixth Day of October, 1987

Attest:

DONALD J. QUIGG

Attesting Officer

Commissioner of Patents and Trademarks